United States Patent [19]

Stoker

[11] Patent Number: 5,476,635
[45] Date of Patent: Dec. 19, 1995

[54] AUTOCLAVE

[75] Inventor: Pieter W. Stoker, Vanderbijlpark, South Africa

[73] Assignee: Excalibur Medical (Proprietary) Limited, South Africa

[21] Appl. No.: 271,143

[22] Filed: Jul. 6, 1994

[51] Int. Cl.⁶ .................................. A61L 2/06; A61L 2/24
[52] U.S. Cl. .......................... 422/26; 422/295; 422/297; 422/110; 99/483
[58] Field of Search ........................... 422/26, 292, 295, 422/297, 300, 302, 304, 307, 119, 110; 99/472, 476, 483

[56] References Cited

U.S. PATENT DOCUMENTS

| | | | |
|---|---|---|---|
| 4,169,408 | 10/1979 | Mencacci | 99/355 |
| 4,195,061 | 3/1980 | Kalasek | 422/302 X |
| 4,646,629 | 3/1987 | Creed et al. | 99/468 |
| 4,707,334 | 11/1987 | Gerhard | 422/304 X |
| 4,773,321 | 9/1988 | Wijts | 422/304 X |

FOREIGN PATENT DOCUMENTS 2452818  5/1976  Germany .
2736088  2/1979  Germany .

*Primary Examiner*—Robert J. Warden
*Assistant Examiner*—Theresa T. Snider
*Attorney, Agent, or Firm*—James Ray & Associates

[57] ABSTRACT

An autoclave 10 has a first vessel 12 in which objects are heated, and a second vessel 14 in which the objects are cooled down. A container 24 containing the objects is introduced via a preheating chamber 30 into a chamber 20, and thence into the cavity 16 of the vessel 12. Similarly, at the downstream end of the second vessel 14, a container is removed from a cavity 18 via a chamber 22. Transfer of containers is effected in a manner similar to operation of a lock to limit loss of pressure. When a container is thus removed and a fresh container is loaded, containers in the cavity 16 are advanced upwardly and containers in the cavity 18 are advanced downwardly. A container at the top of the cavity 16 is laterally displaced to the top of the cavity 18, via a chamber 19. The autoclave is thus operated continuously, stepwise. Pressures and temperatures are monitored via an interface 32 and a computer 34. Sterilization values for the objects are computed and advance of the containers are dependant on appropriate sterilization values being obtained.

18 Claims, 1 Drawing Sheet

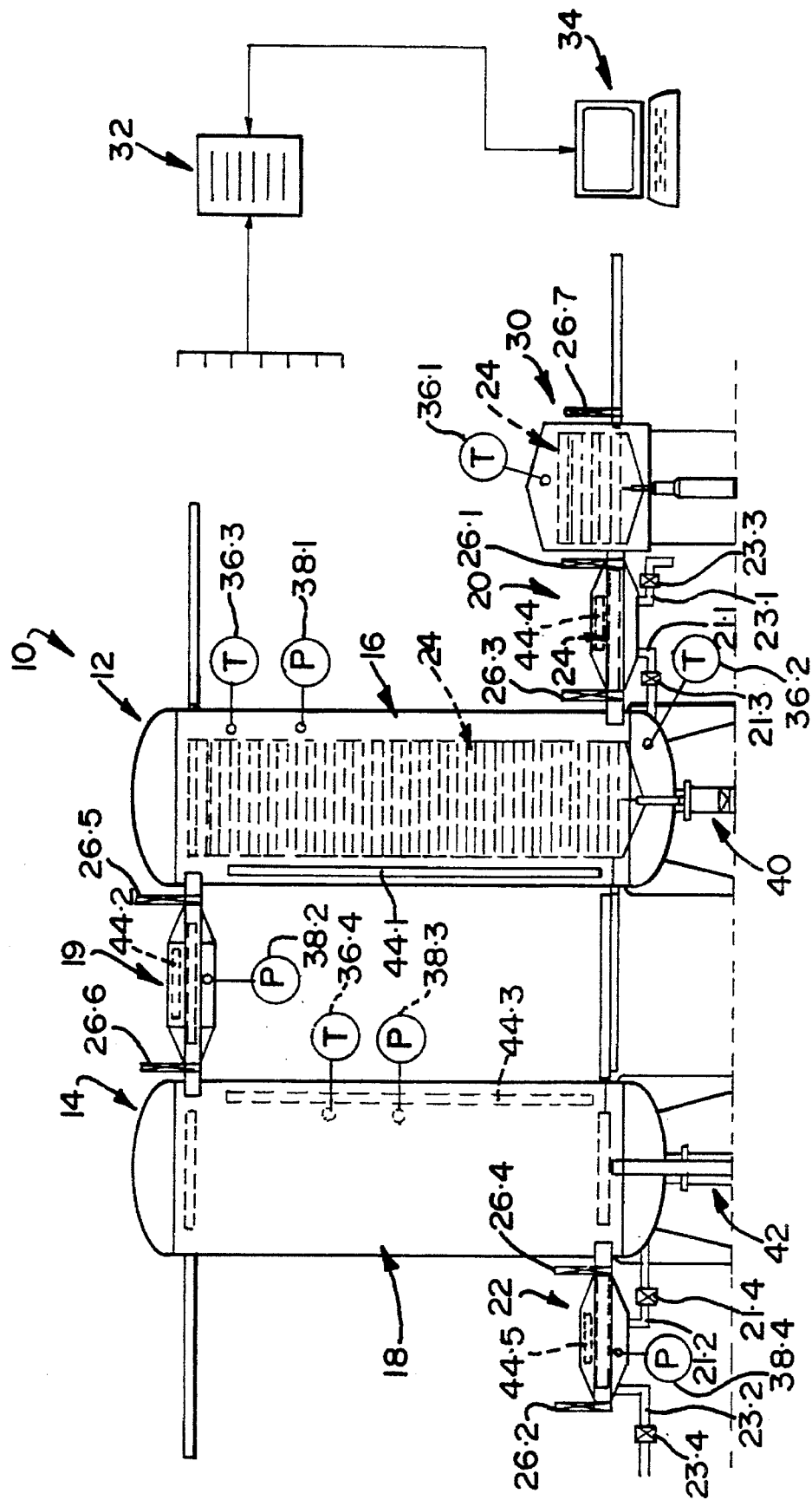

AUTOCLAVE

BACKGROUND OF THE INVENTION

In an autoclave, matter is heated to a high temperature under conditions of high pressure. In one kind of application, matter or objects are thus heated to sterilize the matter or objects.

When an autoclave is batch operated, it is charged with the matter or filled with the objects, closed, and pressurized and heated. After the pressurizing and heating operation, the autoclave is cooled and depressurized, opened and then unloaded.

In known continuous operated autoclaves flowable matter is continuously pumped under high pressure into the autoclave while flowable matter is correspondingly continuously exhausted out of the autoclave.

SUMMARY OF THE INVENTION

In accordance with this invention, broadly, there is provided a method of operating an autoclave for sequentially heating separate objects under pressure and cooling said objects, the method including providing an autoclave having a pre-transfer chamber and a post-transfer chamber, means selectively to communicate the pre-transfer chamber with, and to isolate the pre-transfer chamber from, an operative cavity of the autoclave, means selectively to communicate the post-transfer chamber with, and to isolate the post-transfer chamber from, the operative cavity of the autoclave, and means for selectively pressurizing and depressurizing the respective pre-transfer chamber and post-transfer chamber;

loading an object to be treated into the autoclave by, sequentially, isolating the pre-transfer chamber from the autoclave cavity, depressurizing the pre-transfer chamber, introducing the object into the pre-transfer chamber, isolating the pre-transfer chamber from atmosphere, pressurizing the pre-transfer chamber, communicating the pre-transfer chamber with the autoclave cavity and transferring the object from the pre-transfer chamber into the autoclave cavity; and unloading another object which has been treated from the autoclave by, sequentially, isolating the post-transfer chamber from atmosphere, pressurizing the post-transfer chamber, communicating the post-transfer chamber with the autoclave cavity, transferring said other object into the post-transfer chamber, isolating the post-transfer chamber from the autoclave cavity, depressurizing the post-transfer chamber and removing said other object from the post-transfer chamber.

It is to be appreciated that in respect of both of the pre-transfer chamber and the post-transfer chamber, pressurizing is to a pressure substantially equal to the prevailing pressure in the autoclave cavity.

Isolating the respective pre-transfer chamber and post-transfer chamber from the autoclave cavity may be by closing pressure tight closures between the respective pre-transfer chamber and post-transfer chamber and the autoclave cavity. Communicating the respective pre-transfer chamber and post-transfer chamber with the autoclave cavity may be by opening said pressure might closures, and transferring the respective objects may thus be via openings left open by opening of said pressure tight closures.

Pressurizing each respective chamber may be by inter-communicating it via a restrictive passage with the autoclave cavity.

Advantageously, loading and unloading may be synchronized to take place simultaneously.

In a preferred method, applied in a composite autoclave which includes a first vessel and a second vessel, the pre-transfer chamber being associated with the first vessel and the post-transfer chamber being associated with the second vessel, the method may include progressively moving objects from the pre-transfer chamber through the first vessel, heating said objects in the first vessel, intermittently transferring said objects to the second vessel, cooling said objects in the second vessel and progressively moving said objects through the second vessel toward the post-transfer chamber.

Such intermittent transfer of said objects from the first vessel to the second vessel may be via an intermediate transfer chamber. The method may thus include isolating the intermediate transfer chamber from the second vessel, communicating the intermediate transfer chamber with the first vessel, transferring a respective object from the first vessel to the intermediate transfer chamber, isolating the intermediate transfer chamber from the first vessel, communicating the intermediate transfer chamber with the second vessel and transferring said respective object from the intermediate transfer chamber to the second vessel.

If desired or if required, the method may include operating the second vessel at a pressure different to the pressure of the first vessel. Then, the method may include, after isolating the intermediate transfer chamber from the first vessel, and before communicating the intermediate transfer chamber with the second vessel, equalizing pressures between the second vessel and the intermediate chamber. Equalizing pressures may be effected by exposing the intermediate transfer chamber to the second vessel via a restricted passage.

Advantageously, introducing said object into the pre-transfer chamber may be via a pre-heating chamber. The method may thus include the steps of introducing a respective object into the pre-heating chamber and pre-heating said respective object in the pre-heating chamber. Depressurizing the pre-transfer chamber may include isolating the pre-heating chamber from atmosphere, exposing the pre-transfer chamber to the pre-heating chamber, and relieving the pre-transfer chamber into the pre-heating chamber.

The method may include measuring, at predetermined time intervals, a temperature in the autoclave cavity, comparing the measured temperature with a predetermined base temperature, and adjusting energy input into the autoclave cavity appropriately in response to the difference between the measured temperature and the predetermined base temperature.

Further, the method may include establishing repeatedly, at predetermined time intervals, a temperature of a respective object, computing a sterilization value $F_o$ for said object in accordance with the formula $$F_o = \frac{T}{60} * \sum_{i=1}^{n} 10^{\left(\frac{t_i - t_{ref}}{10}\right)}$$

in which $\triangle T$ is a convenient time interval, for example 10 seconds;

$t_i$ is the average temperature of a product in the i-th time interval;

$t_{ref}$ is a reference temperature namely 121.1° C.;

n is determined such that the sterilization value $F_o$ is bigger than a pre-defined set-point value,
comparing the computed value for $F_o$ with a predetermined base value for $F_o$, and unloading said respective object only when the calculated value for $F_o$ of said respective object is at least equal to the base value for $F_o$.

The method may include measuring the average steam temperature in said operative cavity of the autoclave in which the respective objects are heated, i.e. in the preheating chamber and in the cavity of the first vessel, repeatedly at predetermined time intervals, and computing the value of $t_i$ in accordance with the formula $$t_i = \frac{(t_{i-1} + C * \Delta T * t_{steam\,i})}{(1 + C * \Delta T)}$$

in which $t_i$ is the average temperature of a product in the i-th time interval;

$\Delta T$ is a convenient time interval, for example 10 seconds;

$t_{steam\,i}$ is the average steam temperature as measured in the i-th time interval;

C is an experimentally determined parameter;

$t_{i-1}$ is the average temperature of a product in the i-1 interval.

The method may include recording the $F_o$ value of each object.

The method may then include advancing the objects through the autoclave under control of a computer in accordance with predetermined criteria in respect of positions of respective objects in the autoclave and the values of $F_o$ of the respective objects.

Each object may be in the form of a product contained in a container forming part of the autoclave.

The invention extends to an autoclave for heating, under pressure, separate objects, the autoclave including, a pre-transfer chamber and a post-transfer chamber, means selectively to communicate the pre-transfer chamber with, and to isolate the pre-transfer chamber from, respectively atmosphere and an operative cavity of the autoclave, means selectively to communicate the post-transfer chamber with, and to isolate the post-transfer chamber from, respectively atmosphere and an operative cavity of the autoclave, pressurizing means for selectively pressurizing and depressurizing means for selectively depressurizing the respective pre-transfer chamber and post-transfer chamber, loading means suitable for loading the objects into the pre-transfer chamber, unloading means suitable for unloading the objects from the post-transfer chamber, and transport means suitable for transporting the objects from the pre-transfer chamber through the autoclave cavity to the post-transfer chamber.

Advantageously, the autoclave may be a composite autoclave which includes a first vessel and a second vessel, the operative cavity being defined as sub-cavities in said first vessel and said second vessel, the pre-transfer chamber being associated with the first vessel, and the post-transfer chamber being associated with the second vessel, the autoclave including an intermediate transfer chamber arranged to operate intermediate the first vessel and the second vessel, means selectively to communicate the intermediate transfer chamber with the first vessel and to isolate the intermediate transfer chamber from the first vessel, and means selectively to communicate the intermediate transfer chamber with the second vessel and to isolate the intermediate transfer chamber from the second vessel.

The autoclave may include a plurality of containers suitable to contain the objects, the transport means being adapted for progressively, intermittently in stepped manner, transporting the containers from the pre-transfer chamber through the first vessel, and thence via the intermediate transfer chamber to the second vessel and through the second vessel to the post-transfer chamber. The transport means may be arranged to effect transport along the first vessel upwardly and to effect transport along the second vessel downwardly, the intermediate transfer chamber being arranged intermediate the first vessel and the second vessel at a high level.

The pressurizing means may include pressurizing passages between the autoclave cavity and respectively the pre-transfer chamber and post-transfer chamber and valve means selectively to open and close said pressurizing passages.

The means selectively to communicate each of the pre-transfer chamber and the post-transfer chamber with the operative cavity of the autoclave and to isolate each of the pre-transfer chamber and the post-transfer chamber from the operative cavity of the autoclave may be in the form of openable closures, which are pressure-tight when closed, intermediate the autoclave cavity and respectively the pre-transfer chamber and the post-transfer chamber.

Advantageously, the autoclave may include a pre-heating chamber upstream of the pre-transfer chamber, isolating means arranged selectively to isolate the pre-heating chamber from atmosphere, and lock means arranged selectively to communicate the pre-heating chamber and the pre-transfer chamber and to isolate the pre-heating chamber from the pre-transfer chamber.

The autoclave may include temperature measuring means arranged to measure temperature repeatedly, at predetermined time intervals, in the autoclave, computing means for computing a sterilization value $F_o$ for an object in accordance with the formula $$F_o = \frac{\Delta T}{60} * \sum_{i=1}^{n} 10^{\left(\frac{t_i - t_{ref}}{10}\right)}$$

in which $\Delta T$ is a convenient time interval, for example 10 seconds;

$t_i$ is the average temperature of a product in the i-th time interval;

$t_{ref}$ is a reference temperature namely 121.1° C.;

n is determined such that the sterilization value $F_o$ is bigger than a pre-defined set-point value, and comparing means for comparing the computed value for $F_o$ with a predetermined base value for $F_o$, the unloading means being adapted in response to the result of comparing the computed and base values for $F_o$, to unload the object only when the computed value for $F_o$ is at least equal to the base value for $F_o$.

The computing means may be adapted to compute a value for $t_i$ in accordance with the formula $$t_i = \frac{(t_{i-1} + C * \Delta T * t_{steam\,i})}{(1 + C * \Delta T)}$$

in which $t_i$ is the average temperature of a product in the i-th time interval;

$\Delta T$ is a convenient time interval, for example 10 seconds;

$t_{steam\,i}$ is the average steam temperature as measured in the i-th time interval;

C is an experimentally determined parameter;

$t_{i-1}$ is the average temperature of a product in the i-1 interval.

The autoclave may include computerized control means adapted to actuate the transport means to advance the objects through the autoclave in accordance with predetermined criteria in respect of positions of respective objects in the autoclave and the values of $F_o$ of the respective objects.

The autoclave may include a plurality of containers.

BRIEF DESCRIPTION OF THE DRAWING

The invention is now described by way of example with reference to the accompanying diagrammatic drawing which shows, schematically, in side view, an autoclave in accordance with this invention.

DETAILED DESCRIPTION OF THE PREFERRED EMBODIMENT

With reference to the drawing, an autoclave in accordance with the invention is generally indicated by reference numeral 10. The autoclave 10 is a composite autoclave comprising a first pressure vessel 12 and a second pressure vessel 14. The vessels 12, 14 respectively enclose autoclave cavities generally indicated respectively by reference numerals 16 and 18 which cavities are adapted to be operated under pressure at high temperature. In the embodiment shown, the autoclave is adapted to be operated with steam.

A transversely extending intermediate transfer chamber 19 interconnects the first and second vessels 12, 14 at positions toward upper ends of the vessels.

The vessel 12, more specifically associated with the cavity 16, incorporates heating means for heating the cavity 16. The vessel 14, more specifically associated with the cavity 18, incorporates cooling means for cooling the cavity 18.

Pressurizing means shown diagrammatically respectively at 40, 42 is provided to pressurize the vessels 12, 14.

External to and adjacent to the vessel 12, at a low level and associated with a lower end of the first vessel 12, there is provided a pre-transfer chamber 20. Likewise, external to, and adjacent to the second vessel 14 and associated with a lower end thereof, there is provided a post-transfer chamber 22.

The autoclave 10 has displacement means including a plurality of drawer-like containers 24 and mechanized transport means 44.1 progressively to displace the containers upwardly in the cavity 16, mechanized transport means 44.2 to displace the containers 24 into the intermediate transfer chamber 19 transversely along the intermediate transfer chamber 19 to the top of the cavity 18, mechanized transport means 44.3 progressively to displace the containers 24 downwardly along the cavity 18 to the post-transfer chamber 22. For use with small or flat objects, a container may be divided in upper and lower compartments, each compartment then containing one or more objects.

The pre-transfer chamber 20 and post-transfer chamber 22 are shaped commensurate with and such as to contain containers 24. The containers 24 in use contain objects which are to be heated under pressure in the autoclave 10. Such objects may, for example, be surgical instruments which are to be sterilized for use in an operating theater, drip bags containing water to be sterilized, and the like.

Each of the pre-transfer chamber 20 and the post-transfer 22 has a pressure-tight, openable closure 26.1, 26.2 selectively to open the respective chambers externally or to atmosphere respectively to allow a container 24 to be introduced or loaded into the pre-transfer chamber 20 and such a container to be removed or unloaded from the post-transfer chamber 22.

Furthermore, intermediate the respective autoclave cavities 16, 18 and respectively the pre-transfer chamber 20 and the post-transfer chamber 22, there are provided openable closures 26.3, 26.4 which are pressure tight and which, when open, afford communication between the respective autoclave cavities and respectively the pre-transfer chamber 20 and the post-transfer chamber 22.

It is to be appreciated that, when closed, all of the closures mentioned above are substantially pressure tight.

Pressurizing means is provided in the form of pressurizing passages 21.1, 21.2 between the respective autoclave cavities 16, 18 and respectively the pre-transfer chamber 20 and the post-transfer chamber 22 together with valve means 21.3, 21.4 selectively to render the passages open and closed. Similarly, depressurizing means is provided in the form of depressurizing passages 23.3, 23.4 leading respectively from the pre-transfer chamber 20 and from the post-transfer chamber 22 to vent the respective chambers. The depressurizing passages are provided together with valve means 23.3, 23.4 selectively to render the depressurizing passages open and closed.

When objects to be heated under pressure are to be introduced into the autoclave 10, they are placed within the container 24. The containers 24 are progressively loaded into the autoclave 10. Visualize a specific container 24 containing objects. It is introduced or loaded via the pre-transfer chamber 20 by way of mechanized transport means 44.4 into the cavity 16. In synchronization, a similar container is removed or unloaded from the lower end of the cavity 18 by way of mechanized transport means 44.5 via the post-transfer chamber 22 to remove objects 26 which have already undergone heating under pressure.

Assume that the pre-transfer chamber 20 is in communication with the autoclave cavity 16 and is isolated from atmosphere while the post-transfer chamber 22 is isolated from the autoclave cavity 18 and is open to atmosphere. As a first step, the post-transfer chamber is isolated from atmosphere and the pre-transfer chamber 20 is isolated from the autoclave cavity 16.

To effect loading, the pre-transfer chamber 20 is depressurized by opening the respective depressurizing passage 23.1. The openable closure 26.1 giving external access is then opened, the container 24 is introduced into the chamber 20 and the closure 26.1 is closed.

Unloading is effected by venting the autoclave cavity 18 via the pressurizing passage 21.2 into the post-transfer chamber 22. When the pressures have been equalized, the closure 26.4 giving access from the autoclave cavity 18 into the chamber 22 is opened, and a container 24 is displaced from a bottom of the cavity 18 into the chamber 22. The closure 26.4 is closed.

At that stage, both the chamber 20 and the chamber 22 contain containers and both are isolated from the respective autoclave cavities 16, 18 and from atmosphere.

The pre-transfer chamber 20 is then pressurized to autoclave pressure via the respective pressurizing passage 21.1 by venting the autoclave cavity 16 into the chamber 20. When pressures are equal, the closure 26.3 intermediate the autoclave cavity 16 and the chamber 20 can be opened and the container 24 containing the objects 26 is introduced into the autoclave cavity 16 at the bottom thereof.

More or less simultaneously, the chamber 22 is depressurized by venting it to atmosphere via the depressurizing passage 23.2 and the drawer is unloaded by opening the external closure 26.2.

Associated with loading and unloading, in the cavity 16, the containers 24 have been moved up one position each and the containers 24 in the cavity 18 have been moved down one position each. The top container in the cavity 16 has been displaced into the intermediate transfer chamber 19, has been displaced laterally through the intermediate transfer chamber 19 and has been displaced downwardly to the top of the second portion 16. Such displacing is effected in a manner similar to operations of a lock via the closures 26.5 and 26.6 by first opening the closure 26.5 while the closure 26.6 remains closed and displacing the top container in the cavity 16 into the intermediate transfer chamber 19; and the closing the closure 26.5, thereafter opening the closure 26.6 and displacing the container from the intermediate transfer chamber 19 into the cavity 18; and, if required, by equalizing pressures firstly between the chamber 19 and the cavity 16, and secondly between the chamber 19 and the cavity 18.

The above procedure is intermittently repeated, to introduce containers containing fresh objects into the autoclave and to remove containers containing treated objects from the autoclave. The procedure is controlled, as described below, to ensure the required degree of sterilizing.

The autoclave cavity is repressurized from time to time to maintain its pressure within predetermined limits. Heating is controlled to maintain appropriately high temperatures.

Advantageously, there is provided a preheating chamber 30 upstream of the pre-transfer chamber 20. The preheating chamber 30 has capacity to contain a plurality of containers 24. The closure 26.1 is arranged selectively to communicate the preheating chamber 30 and the pre-transfer chamber 20, and to isolate them. In addition, there is provided a closure 26.7 intermediate the preheating chamber 30 and atmosphere.

Thus, by closing the closure 26.1, the preheating chamber 30 is isolated from the autoclave 10 to allow loading of fresh containers 24. After loading, the preheating chamber 30 is isolated from atmosphere by closing the closure 26.7 to allow the containers in waiting to be preheated prior to being loaded into the autoclave 10 via the pre-transfer chamber 20.

Preheating is effected, if desired, by providing heating means associated with the preheating chamber. Pre-heating is facilitated conveniently by depressurizing the pre-transfer chamber 20 via an appropriate passage and valve means into the preheating chamber 30 to re-use the energy which would otherwise have been lost.

Apart from using waste energy, the use of the preheating chamber has the advantages that the thermal shock on the autoclave cavity 16 when loading takes place is diminished and that the objects preheated are brought to elevated temperatures in the cavity 16 quicker than would otherwise have been possible thus enhancing the capacity of the autoclave 10.

It is extremely important that operation of the autoclave 10 be managed or controlled automatically by means of a computer. It is further of paramount importance that such control be based primarily on computing a sterilization value $F_o$ (as described above) in respect of the objects in each container and controlling advance of the objects or the containers through the autoclave on actual sterilization values achieved in use. Furthermore, temperature control in the autoclave cavity 16 is based on the sterilization values measured in comparison to base sterilization values.

Thus, control of operation of the autoclave 10 is via an interface 32 by means of a computer 34.

Control commences with compiling of information regarding pressure and temperature at strategic positions through the autoclave, more specifically, in respect of temperature, in the preheating chamber as shown at "T" 36.1, in the autoclave cavity 16 as shown at "T" 36.2 and "T" 36.3, and the autoclave cavity 18 as shown at "T" 36.4. Monitoring of pressure is important in respect of transport, in the manner of a lock, of the containers and is monitored in the autoclave cavity 16 as shown at "P" 38.1, the intermediate transfer chamber 19 as shown at "P" 38.2, the autoclave cavity 18 as shown at "P" 38.3 and the post-transfer chamber 22 as shown at "P" 38.4.

As described above, the sterilization value or $F_o$ value for each container is computed based on data actually measured and progression of the sterilization process, or advance of the containers through the autoclave 10, is controlled in accordance with comparisons between actual sterilization values achieved and predetermined base values for sterilization values which are predetermined.

By means of the computer 34, via the interface 32, the valves for controlling pressurization and depressurization, hydraulic or pneumatic cylinders for opening and closing closures, and the transport means, are controlled.

It is an advantage of the invention that an autoclave in accordance with the invention can receive fresh objects and can exhaust treated objects on a substantially continuous albeit stepwise fashion. It is further an advantage that less energy is required to maintain the pressure in the autoclave cavity as, first, only a relatively small chamber is depressurized and pressurized in respect of each loading and unloading operation. It is an important advantage that the autoclave can be operated on a continuous basis as opposed to batch operation.

It is further an advantage that objects to be sterilized are advanced and are ultimately unloaded from the autoclave only in response to appropriate results obtained from automated monitoring of the sterilization value to ensure adequate or appropriate sterilization of the products.

I claim:

1. A method of operating an autoclave for sequentially heating separate objects under pressure and cooling said objects, the method comprising:

providing an autoclave having a pre-transfer chamber and a post-transfer chamber, means selectively to communicate the pre-transfer chamber with, and to isolate the pre-transfer chamber from, an operative cavity of the autoclave, means selectively to communicate the post-transfer chamber with, and to isolate the post-transfer chamber from, the operative cavity of the autoclave, means for selectively pressurizing respectively the pre-transfer chamber and the post-transfer chamber and means for selectively depressurizing respectively the pre-transfer chamber and the post-transfer chamber;

loading an object to be treated into the autoclave by, sequentially, isolating the pre-transfer chamber from the operative cavity, depressurizing the pre-transfer chamber, introducing the object into the pre-transfer chamber, isolating the pre-transfer chamber from atmosphere, pressurizing the pre-transfer chamber, communicating the pre-transfer chamber with the operative cavity and transferring the object from the pre-transfer chamber into the operative cavity; and unloading another object which has been treated from the autoclave by, sequentially, isolating the post-transfer chamber from atmosphere, pressurizing the post-transfer chamber, communicating the post-transfer chamber with the operative cavity, transferring said other object into the post-transfer chamber, isolating the post-transfer chamber from the operative cavity, depressurizing the post-transfer chamber and removing said other object from the post-transfer chamber, the method further including establishing repeatedly, at predetermined time intervals, a temperature of a respective object, computing a sterilization value $F_o$ for said object in accordance with the formula $$F_o = \frac{T}{60} * \sum_{i=1}^{n} 10^{\frac{t_i - t_{ref}}{10}}$$

in which $\triangle T$ is a convenient time interval;

$t_i$ is the average temperature of a product in the th time interval;

$t_{ref}$ is a reference temperature;

n is determined such that the sterilization value $F_o$ is bigger than a pre-defined set-point value, comparing the computed value for $F_o$ with a predetermined base value for $F_o$, and unloading said respective object only when the calculated value for $F_o$ of said respective object is at least equal to the base value for $F_o$.

2. A method as claimed in claim 1 which includes measuring the average steam temperature, in said operative cavity of the autoclave in which the respective objects are heated, repeatedly at predetermined time intervals, and computing the value of $t_i$ in accordance with the formula $$t_i = \frac{(t_{i-1} + C * \triangle T * t_{steam\ i})}{(1 + C * \triangle T)}$$

in which $t_i$ is the average temperature of a product in the i-th time interval;

$\triangle T$ is a convenient time interval;

$t_{steam\ i}$ is the average steam temperature as measured in the i-th time interval;

C is an experimentally determined parameter;

$t_{i-1}$ is the average temperature of a product in the i-1 interval.

3. A method as claimed in claim 1 which includes recording the $F_o$ value of each object.

4. A method as claimed in claim 1 which includes advancing the objects through the autoclave under control of a computer in accordance with predetermined criteria in respect of positions of respective objects in the autoclave and the values of $F_o$ of the respective objects.

5. An autoclave for heating, under pressure, separate objects, the autoclave comprising:

a pre-transfer chamber and a post-transfer chamber, means selectively to communicate the pre-transfer chamber with, and to isolate the pre-transfer chamber from, an operative cavity of the autoclave, means selectively to communicate the post-transfer chamber with, and to isolate the post-transfer chamber from, the operative cavity of the autoclave, means for selectively pressurizing respectively the pre-transfer chamber and the post-transfer chamber and means for selectively depressurizing respectively the pre-transfer chamber and the post-transfer chamber, loading means suitable for loading the objects into the pre-transfer chamber, unloading means suitable for unloading the objects from the post-transfer chamber, transport means suitable for transporting the objects from the pre-transfer chamber through the autoclave cavity to the post-transfer chamber, temperature measuring means in the operative cavity to measure temperature repeatedly, at predetermined time intervals, in the autoclave, a computer for computing sterilization values $F_o$ for objects being sterilized in accordance with the formula $$F_o = \frac{T}{60} * \sum_{i=1}^{n} 10^{\frac{t_i - t_{ref}}{10}}$$

in which $\triangle T$ is a convenient time interval;

$t_i$ is the average temperature of a product in the th time interval;

$t_{ref}$ is a reference temperature;

n is determined such that the sterilization value $F_o$ is bigger than a pre-defined set-point value, and for comparing the computed value for $F_o$ with a predetermined base value for $F_o$, the unloading means being controllable in response to the result of comparing the computed and base values for $F_o$, to unload the object only when the computed value for $F_o$ is at least equal to the base value for $F_o$.

6. An autoclave as claimed in claim 5 in which the computer is programmed to compute a value for $t_i$ in accordance with the formula $$t_i = \frac{(t_{i-1} + C * \triangle T * t_{steam\ i})}{(1 + C * \triangle T)}$$

in which $t_i$ is the average temperature of a product in the i-th time interval;

$\triangle T$ is a convenient time interval, for example 10 seconds;

$t_{steam\ i}$ is the average steam temperature as measured in the i-th time interval;

C is an experimentally determined parameter;

$t_{i-1}$ is the average temperature of a product in the i-1 interval.

7. An autoclave as claimed in claim 5 which includes computerized control means programmed to actuate the transport means to advance the objects through the autoclave in accordance with predetermined criteria in respect of positions of respective objects in the autoclave and the values of $F_o$ of the respective objects.

8. A method of operating an autoclave for sequentially heating separate objects under pressure and cooling said objects, the method comprising:

providing an autoclave having a pre-transfer chamber and a post-transfer chamber, means selectively to communicate the pre-transfer chamber with, and to isolate the pre-transfer chamber from, an operative cavity of the autoclave, means selectively to communicate the post-transfer chamber with, and to isolate the post-transfer chamber from, the operative cavity of the autoclave, pressurizing means for selectively pressurizing respectively the pre-transfer chamber and the post transfer chamber and depressurizing means for selectively depressurizing respectively the pre-transfer chamber and the post-transfer chamber, said pressurizing means comprising a first restrictive passage having first valve means between the operative cavity and the pre-transfer chamber and a second restrictive passage having second valve means between the operative cavity and the post-transfer chamber, said depressurizing means comprising a third restrictive passage having third valve means extending from the pre-transfer chamber and a fourth restrictive passage having fourth valve means extending from the post-transfer chamber;

loading an object to be treated into the autoclave by, sequentially, isolating the pre-transfer chamber from the operative cavity, depressurizing the pre-transfer chamber by opening the third valve means in the third restrictive passage, introducing the object into the pre-transfer chamber, isolating the pre-transfer chamber from atmosphere, pressurizing the pre-transfer chamber via said first restrictive passage between the operative cavity and the pre-transfer chamber by opening said first valve means of said first restrictive passage, communicating the pre-transfer chamber with the operative cavity and transferring the object from the pre-transfer chamber into the operative cavity; and unloading another object which has been treated from the autoclave by, sequentially, isolating the post-transfer chamber from atmosphere, pressurizing the post-transfer chamber via said second restrictive passage between the operative cavity and the post transfer chamber by opening said second valve means of said second restrictive passage, communicating the post-transfer chamber with the operative cavity, transferring said other object into the post-transfer chamber, isolating the post-transfer chamber from the operative cavity, depressurizing the post-transfer chamber by opening the fourth valve means of the fourth restrictive passage of the depressurizing means and removing said other object from the post-transfer chamber.

9. A method of operating an autoclave for sequentially heating separate objects under pressure and cooling said objects, the method comprising:

providing a composite autoclave which includes a first vessel and a second vessel, an operative cavity of the autoclave being defined as sub-cavities in said first and second vessels, a pre-transfer chamber adjacent the first vessel, a pressure tight closure which is selectively openable to communicate the pre-transfer chamber with the first vessel and which is selectively closeable to isolate the pre-transfer chamber from the first vessel, pressurizing means for selectively pressurizing the pre-transfer chamber and depressurizing means for selectively depressurizing the pre-transfer chamber, a post-transfer chamber adjacent the second vessel, a pressure tight closure which is selectively openable to communicate the post-transfer chamber with the second vessel and which is selectively closeable to isolate the post-transfer chamber from the second vessel, pressurizing means for selectively pressurizing the post-transfer chamber and depressurizing means for selectively depressurizing post-transfer chamber;

loading an object to be treated into the autoclave by, sequentially, isolating the pre-transfer chamber from the operative cavity depressurizing the pre-transfer chamber, introducing the object into the pre-transfer chamber, isolating the pre-transfer chamber from atmosphere, pressurizing the pre-transfer chamber, communicating the pre-transfer chamber with the operative cavity and transferring the object from the pre-transfer chamber into the operative cavity; progressively moving objects from the pre-transfer chamber through the first vessel, heating said objects in the first vessel, intermittently transferring said objects to the second vessel, cooling said objects in the second vessel and progressively moving said objects through the second vessel towards the post-transfer chamber; and unloading another object which has been treated from the autoclave by, sequentially, isolating the post-transfer chamber from atmosphere, pressurizing the post-transfer chamber, communicating the post transfer chamber with the operative cavity, transferring said other object into the post-transfer chamber, isolating the post-transfer chamber from the operative cavity, depressurizing the post-transfer chamber and removing said other object from the post transfer chamber.

10. A method as claimed in claim 9, in which intermittent transfer of said objects from the first vessel to the second vessel is via an intermediate transfer chamber, the method including isolating the intermediate transfer chamber from the second vessel, communicating the intermediate transfer chamber with the first vessel, transferring a respective object from the first vessel to the intermediate transfer chamber, isolating the intermediate transfer chamber from the first vessel, communicating the intermediate transfer chamber with the second vessel and transferring said respective object from the intermediate transfer chamber to the second vessel.

11. A method as claimed in claim 10 which includes operating the second vessel at a pressure different than the pressure of the first vessel.

12. A method as claimed in claim 11 which includes, after isolating the intermediate transfer chamber from the first vessel, and before communicating the intermediate transfer chamber with the second vessel, equalizing pressures between the second vessel and the intermediate chamber.

13. A method as claimed in claim 12 in which equalizing pressures is effected by providing a restrictive passage having valve means between the intermediate transfer chamber and the second vessel and opening said valve means.

14. An autoclave for heating, under pressure, separate objects, the autoclave comprising:

a pre-transfer chamber and a post-transfer chamber, means selectively to communicate the pre-transfer chamber with, and to isolate the pre-transfer chamber from, atmosphere and an operative cavity of the autoclave; means selectively to communicate the post-transfer chamber with, and to isolate the post-transfer chamber from, atmosphere and the operative cavity of the autoclave; pressurizing means for selectively pressurizing respectively the pre-transfer chamber and the post transfer chamber; depressurizing means for selectively depressurizing respectively the pre-transfer chamber and the post-transfer chamber, said pressurizing means comprising a first restrictive passage having first valve means between the operative cavity and the pre-transfer chamber and a second restrictive passage having second valve means between the autoclave cavity and the post-transfer chamber, said depressurizing means comprising a third restrictive passage having third valve means extending from the pre-transfer chamber and a fourth restrictive passage having fourth valve means extending from the post-transfer chamber;

loading means suitable for loading the objects into the pre-transfer chamber; unloading means suitable for unloading the objects from the post-transfer chamber; and transport, means suitable for transporting the objects from the pre-transfer chamber through the autoclave cavity to the post-transfer chamber.

15. An autoclave for heating, under pressure, separate objects, the autoclave being a composite autoclave comprising:

a first vessel and a second vessel, an operative cavity of the autoclave being defined as sub-cavities in said first and second vessels, a pre-transfer chamber adjacent the first vessel, a pressure tight closure which is selectively openable to communicate the pre-transfer chamber with the first vessel and which is selectively closeable to isolate the pre-transfer chamber from the first vessel, pressurizing means for selectively pressurizing the pre-transfer chamber and depressurizing means for selectively depressurizing the pre-transfer chamber, a post-transfer chamber adjacent the second vessel, a pressure tight closure which is selectively openable to communicate the post-transfer chamber with the second vessel and which is selectively closeable to isolate the post-transfer chamber from the second vessel, pressurizing means for selectively pressurizing the post-transfer chamber and depressurizing means for selectively depressurizing post-transfer chamber, an intermediate transfer chamber arranged to operate in the manner of a lock intermediate the first vessel and the second vessel, means selectively to communicate the intermediate transfer chamber with each of the first vessel and the second vessel and to isolate the intermediate transfer chamber from each of the first vessel and the second vessel, loading means suitable for loading the objects into the pre-transfer chamber, unloading means suitable for unloading the objects from the post-transfer chamber, and transport means suitable for transporting the objects from the pre-transfer chamber through the operative cavity to the post-transfer chamber.

16. An autoclave as claimed in claim 15 which has pressurizing means for the first and second vessels and which is operable to pressurize the second vessel at a pressure different to the pressure of the first vessel, the autoclave having pressure equalizing means selectively operable between the intermediate transfer chamber and the second vessel.

17. An autoclave as claimed in claim 15 which includes a plurality of containers suitable to contain the objects, the transport means being controllable for progressively, intermittently in stepped manner, transporting the containers from the pre-transfer chamber through the first vessel, and thence via the intermediate transfer chamber to the second vessel and through the second vessel to the post-transfer chamber.

18. An autoclave as claimed in claim 17 in which the transport means is arranged to effect transport along the first vessel upwardly and to effect transport along the second vessel downwardly, the intermediate transfer chamber being arranged intermediate the first vessel and the second vessel at a level which is higher than the pre-transfer chamber and the post-transfer chamber.

* * * * *